United States Patent
Chiou et al.

(10) Patent No.: US 10,829,802 B2
(45) Date of Patent: Nov. 10, 2020

(54) MEASURING METHOD FOR AMPLICON LENGTH

(71) Applicant: Quark Biosciences Taiwan, Inc., Hsinchu County (TW)

(72) Inventors: Chung-Fan Chiou, Hsinchu County (TW); Cheng-Wey Wei, Hsinchu County (TW); Yu Chang, Hsinchu County (TW); Chang-Wei Huang, Hsinchu County (TW)

(73) Assignee: Quark Biosciences Taiwan, Inc., Hsinchu County (TW)

( * ) Notice: Subject to any disclaimer, the term of this patent is extended or adjusted under 35 U.S.C. 154(b) by 1163 days.

(21) Appl. No.: 14/938,823

(22) Filed: Nov. 11, 2015

(65) Prior Publication Data

US 2017/0058330 A1  Mar. 2, 2017

(30) Foreign Application Priority Data

Aug. 24, 2015  (TW) .............................. 104127429 A (51) Int. Cl.
 C12Q 1/6818  (2018.01)
 C12Q 1/6851  (2018.01)
(52) U.S. Cl.
 CPC ......... *C12Q 1/6818* (2013.01); *C12Q 1/6851* (2013.01)

(58) Field of Classification Search
 None
 See application file for complete search history.

(56) References Cited

FOREIGN PATENT DOCUMENTS

| CN | 1427895 | 7/2003 |
|---|---|---|
| CN | 101381766 | 3/2009 |
| CN | 103173560 | 6/2013 |
| CN | 103184279 | 7/2013 |
| TW | I342949 | 6/2011 |

OTHER PUBLICATIONS

Laurie et al., "Simultaneous digital quantification and fluorescence-based size characterization of massively parallel sequencing libraries," BioTechniques, Aug. 2013, pp. 61-67.
Shui-Fang Zhu, et al., "Chapter 9 Quantitative detection of genetically-modified products by real-time fluorescent PCR" Detection Techniques of Genetically-Modified Plant Products, Guangdong Science and Technology Press, Apr. 2003, pp. 123-129.

*Primary Examiner* — Joseph Woitach
(74) *Attorney, Agent, or Firm* — JCIPRNET (57) ABSTRACT

A measuring method for amplicon length is provided. A qPCR master mix, a forward primer, a reverse primer, a hybridization probe, a double-stranded DNA binding dye, and nucleic acid samples are added into reaction wells for qPCR reaction, and the fluorescence intensity of each of a hybridization probe and a double-stranded DNA binding dye varying with cycle number is respectively measured. Afterwards, amplicon length is obtained by applying a calculating method.

10 Claims, 6 Drawing Sheets

| Respectively converting the fluorescence intensity of the double-stranded DNA binding dye and the fluorescence intensity of the hybridization probe measured for each of the amplicons into a normalized fluorescence intensity of the double-stranded DNA binding dye and a normalized fluorescence intensity of the hybridization probe | — S340 |

| Divide the normalized fluorescence intensity of the double-stranded DNA binding dye and the normalized fluorescence intensity of the hybridization probe of each of the amplicons by each other to obtain a fluorescence intensity ratio | — S350 |

| Substitute the fluorescence intensity ratio of each of the amplicons at a threshold cycle number in the linear regression curve of fluorescence intensity ratio and amplicon length to calculate the length of each of the amplicons | — S360 |

MEASURING METHOD FOR AMPLICON LENGTH

CROSS-REFERENCE TO RELATED APPLICATION

This application claims the priority benefit of Taiwan application serial no. 104127429, filed on Aug. 24, 2015. The entirety of the above-mentioned patent application is hereby incorporated by reference herein and made a part of this specification.

BACKGROUND OF THE INVENTION

Field of the Invention

The invention relates to a measuring method, and more specifically, to a measuring method of amplicon length.

Description of Related Art

In the field of molecular biology, sequencing is performed on a nucleic acid target (such as DNA or RNA) in order to determine its correct base arrangement; the resulting information provides genetic information of a particular gene of a particular sample. The development of gene sequencing accelerates the research and the discovery of biology and medicine, as it is extensively applied in the fields of molecular diagnostics, biological technology, forensic science, and biosystematics.

In recent years, the development of next-generation sequencing (NGS) technique significantly reduces sequencing cost and time. Prior to subjecting a sample for NGS analysis, a library of nucleic acids, which have adaptors of known sequence attached to both terminals, is built. In addition, two essential steps prior to subjecting a library for NGS detection are 1) the determination of the concentration and 2) the determination of the length distribution of the library. When the concentration of the NGS library is too high due to high cluster density, the quality of NGS data will be poor. On the other hand, when the concentration of the NGS library is too low due to low cluster density, the NGS data will be compromised. Moreover, if the length distribution in the NGS library is too broad, then the read depth may be too low. Therefore, in the operating process of an NGS technique, immediately prior to the step of machine operation, quality control needs to be performed to confirm the length distribution and the concentration of the NGS library.

Currently, the concentration of the NGS library is mostly determined via a qPCR (real-time PCR) technique, while the length distribution of the NGS library is deciphered via capillary electrophoresis (CE). However, a standard curve needs to be generated for the qPCR technique, and therefore creating a more complex experimental procedure. CE has multiple disadvantages, one of which is low sensitivity. Moreover, the fragment length and the concentration of the NGS library need to be determined by two separate experimental procedures, such that the cost and the time needed are readily increased. Therefore, the development of a measuring method capable of accurately and simultaneously analyzing both the length distribution and the concentration of NGS library is an important object for those skilled in the art.

SUMMARY OF THE INVENTION

The invention provides a measuring method for amplicon length capable of accurately and simultaneously analyzing both the length and the concentration of amplicon in nucleic acid samples. More specifically, when the content of a next-generation sequencing (NGS) library is amplified via a qPCR technique, the enlarged nucleic acid product of the NGS library is an amplicon, and in the invention, the length distribution and the concentration of the NGS library are further calculated via the determination of the length and the concentration of amplicon.

The invention provides a measuring method for amplicon length including the following steps. First, a qPCR master mix, a forward primer, a reverse primer, a hybridization probe, a double-stranded DNA binding dye, and extremely-diluted (3 copies/μl to 30 copies/μl) nucleic acid samples are mixed to form a qPCR reaction mixture. Then, the qPCR reaction mixture is distributed in the reaction wells of a test slide, and no more than one nucleic acid sample is distributed in each of the reaction wells. Then, a qPCR reaction is performed on the qPCR reaction mixture to measure 1) the fluorescence intensity of each of the hybridization probe varying with the number of reaction cycles and 2) the fluorescence intensity of each of the double-stranded DNA binding dye varying with the number of reaction cycles, of which the varying fluorescence intensity of the hybridization probe and double-stranded DNA binding dye are dependent on the concentration and the length of each amplicon, respectively, in the nucleic acid samples. A calculating method is then applied to calculate the length of each of the amplicons.

In an embodiment of the invention, the calculating method includes defining a threshold value in the fluorescence intensity of the hybridization probe measured for each of the amplicons, and correspondingly obtaining the threshold cycle number of each of the amplicons when the fluorescence intensity of the hybridization probe is the threshold value. Then, the individual fluorescence intensity of the double-stranded DNA binding dye of each of the amplicons at the threshold cycle number is correspondingly obtained. The intensity of individual fluorescence is substituted in the linear regression curve of the fluorescence intensity of the double-stranded DNA binding dye and amplicon length to calculate the length of each of the amplicons.

In an embodiment of the invention, the calculating method includes respectively converting the fluorescence intensity of the double-stranded DNA binding dye and the fluorescence intensity of the hybridization probe measured for each of the amplicons into a normalized fluorescence intensity of the double-stranded DNA binding dye and a normalized fluorescence intensity of the hybridization probe. Then, the normalized fluorescence intensity of the double-stranded DNA binding dye and the normalized fluorescence intensity of the hybridization probe of each of the amplicons are divided by each other to obtain a fluorescence intensity ratio. Then, the fluorescence intensity ratio of each of the amplicons at the threshold cycle number is substituted in the linear regression curve of fluorescence intensity ratio and amplicon length to calculate the length of each of the amplicons.

In an embodiment of the invention, the converting method of the normalized fluorescence intensity of the double-stranded DNA binding dye and the normalized fluorescence intensity of the hybridization probe includes dividing the fluorescence intensity of the double-stranded DNA binding dye at each cycle by the average fluorescence intensity of the double-stranded DNA binding dye in a cycle interval to calculate the normalized fluorescence intensity of the double-stranded DNA binding dye. The fluorescence intensity of the hybridization probe at each cycle is divided by the average fluorescence intensity of the hybridization probe in the cycle interval to obtain the normalized fluorescence intensity of the hybridization probe.

In an embodiment of the invention, the double-stranded DNA binding dye includes an SYBR Green dye, an Eva Green dye, an LC Green dye, or an SYTO 9 dye.

In an embodiment of the invention, the threshold value is 1.1 to 1.5.

In an embodiment of the invention, the qPCR master mix includes a reaction buffer, dNTP, $MgCl_2$, and Taq polymerase.

In an embodiment of the invention, the concentration of the double-stranded DNA binding dye in the qPCR reaction mixture is 1 uM to 10 uM.

In an embodiment of the invention, the concentration of the hybridization probe in the qPCR reaction mixture is 0.2 uM to 1 uM.

In an embodiment of the invention, the concentration of the forward primer in the qPCR reaction mixture is 0.03 uM to 0.5 uM, and the concentration of the reverse primer in the qPCR reaction mixture is 0.03 uM to 0.5 uM.

In an embodiment of the invention, the volume ratio of the nucleic acid samples and the qPCR reaction mixture is 1:60 to 1:10.

In an embodiment of the invention, the hybridization probe includes a TaqMan probe, a molecular beacon probe, a dual-hybridization probe, or an Eclipse probe.

In an embodiment of the invention, the nucleic acid samples include a NGS library.

Based on the above, in the measuring method for amplicon length provided by the invention, a hybridization probe (related to the concentration of amplicon) and a double-stranded DNA binding dye (related to the length of amplicon) are both added into a qPCR reaction mixture at the same time to perform a qPCR reaction, so as to respectively measure the fluorescence intensity of each of the hybridization probe and the double-stranded DNA binding dye varying with cycle number to correspondingly obtain the threshold cycle number of amplicon, and thereby calculate the length of amplicon. Therefore, the measuring method for amplicon length provided by the invention can accurately and simultaneously analyze both the length and the concentration of amplicon in nucleic acid samples and be applied in the quality control of NGS technique.

In order to make the aforementioned features and advantages of the disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
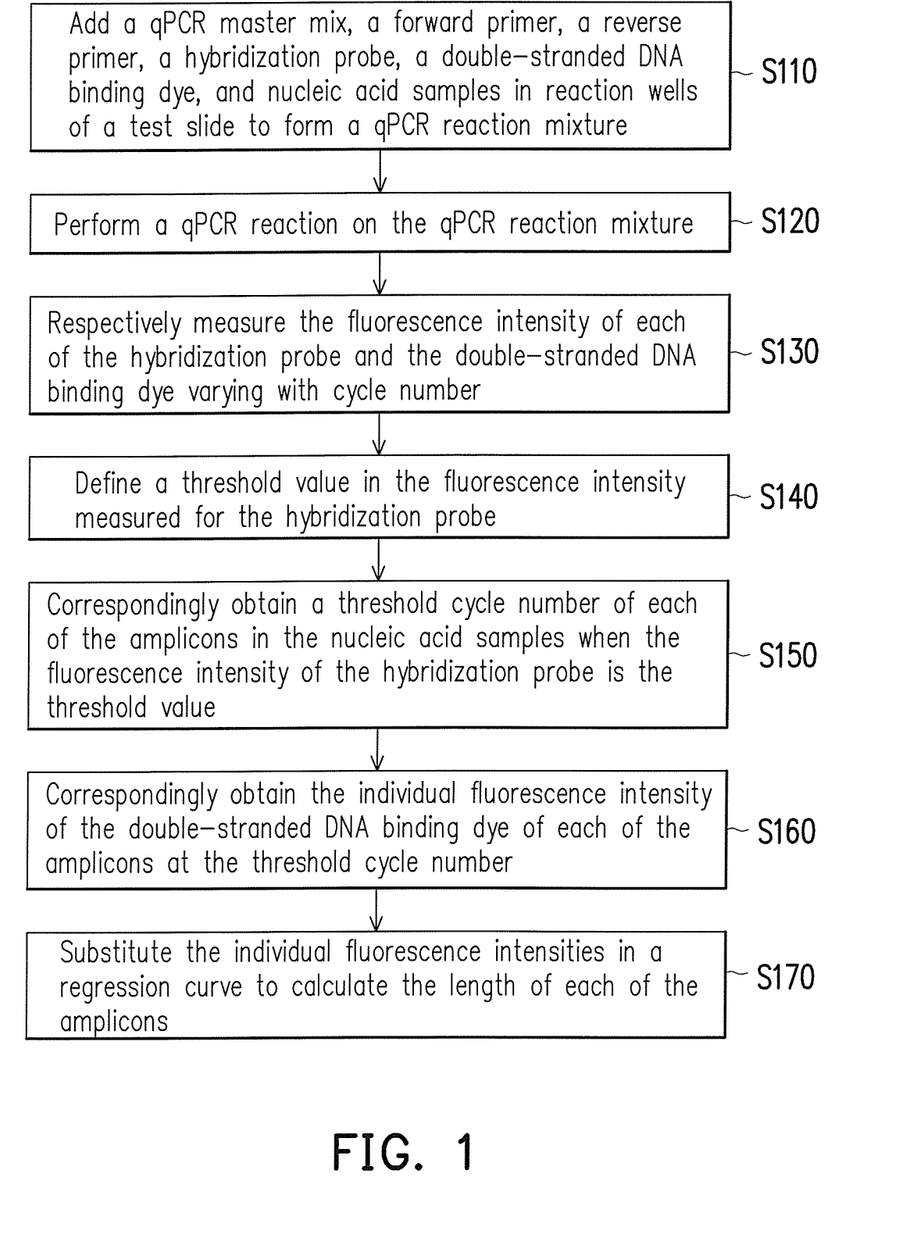
FIG. 1 is a schematic flow chart of a measuring method for amplicon length according to an embodiment of the invention.
Figure 2:
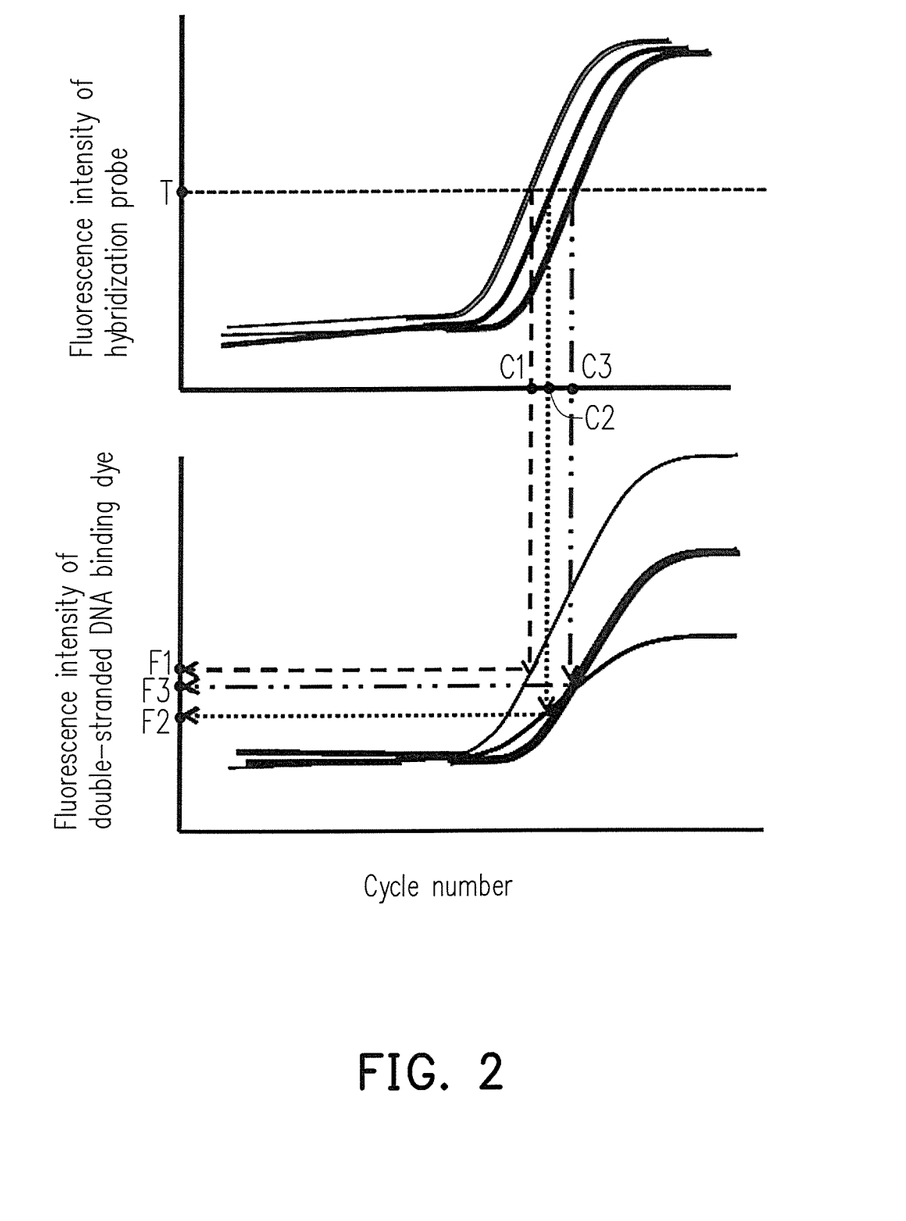
FIG. 2 is a graph of the fluorescence intensity of each of a hybridization probe and a double-stranded DNA binding dye varying with cycle number measured in the measuring method for amplicon length according to an embodiment of the invention.

FIG. 1 is a schematic flow chart of a measuring method for amplicon length according to an embodiment of the invention. FIG. 2 is a graph of the fluorescence intensity of each of a hybridization probe and a double-stranded DNA binding dye varying with cycle number measured in the measuring method for amplicon length according to an embodiment of the invention. In the following, the measuring method for amplicon length according to an embodiment of the invention is described in detail with FIG. 1 and FIG. 2.

Referring to FIG. 1, step S110 is first performed, in which a qPCR master mix, a forward primer, a reverse primer, a hybridization probe, a double-stranded DNA binding dye, and nucleic acid samples are added in the reaction wells of a test slide to form a qPCR reaction mixture. The test slide can be a slide plate having a plurality of reaction wells, and a qPCR reaction can be performed in each of the reaction wells.

More specifically, in the formed qPCR reaction mixture, the concentration of the forward primer is, for instance, 0.03 uM to 0.5 uM, the concentration of the reverse primer is, for instance, 0.03 uM to 0.5 uM, the concentration of the double-stranded DNA binding dye is, for instance, 1 uM to 10 uM, and the concentration of the hybridization probe is, for instance, 0.2 uM to 1 uM.

In the present embodiment, the double-stranded DNA binding dye can include an SYBR Green dye, an Eva Green dye, an LC Green dye, or an SYTO 9 dye, and is preferably an Eva Green dye, but the invention is not limited thereto, and other fluorescent dyes capable of binding with double-stranded DNA can also be used. More specifically, the additive amount of the double-stranded DNA binding dye is, for instance, greater than the known additive amount of a qPCR reaction by 1× concentration to 5× concentrations. The hybridization probe can include a TaqMan probe, a molecular beacon probe, a dual-hybridization probe, or an Eclipse probe, but the invention is not limited thereto, and other fluorescent dyes capable of emitting one fluorescent signal at each DNA replication cycle can also be used.

In the present embodiment, the volume ratio of the nucleic acid samples and the qPCR reaction mixture is, for instance, 1:60 to 1:10. The nucleic acid samples can include a next-generation sequencing (NGS) library, that is, the measuring method for amplicon length provided by the invention can be applied in the quality control of NGS technique, but is not limited thereto, and the measuring method provided by the invention can also be applied in any other techniques requiring accurate analysis of the length and the concentration of amplicon.

In the present embodiment, the qPCR master mix can adopt a commercial product, and can include a reaction buffer, dNTP, $MgCl_2$, and Taq polymerase. A commercial product of the qPCR master mix can include, for instance, QuantiTect Probe PCR Kit of Qiagen, TaqMan Gene Expression Master Mix of Applied Biosystems, iTaq Supennix with ROX of Bio-Rad, or Express qPCR SuperMix of Invitrogen, but the invention is not limited thereto. More specifically, when the qPCR reaction mixture is formed, the concentration of the qPCR master mix is, for instance, 1× concentration.

Then, referring further to FIG. 1, step S120 is performed, in which a qPCR reaction is performed on the qPCR reaction mixture formed in the reaction wells of the test slide in step S110. The operating condition settings of the qPCR reaction can be comparable to the operating settings of a known qPCR reaction. For instance, a reaction is first performed at 50° C. for 2 minutes, then a reaction is performed at 95° C. for 3 minutes to perform a Taq polymerase hot start step, and then 40 times of the following cycle are performed: performing a reaction at 95° C. for 36 seconds and performing a reaction at 60° C. for 72 seconds, but the invention is not limited thereto, and the operating settings of the qPCR reaction can also be adjusted according to actual demand.

Then, referring to both FIG. 1 and FIG. 2, as shown in FIG. 1, step S130 is performed, in which the fluorescence intensity of each of the hybridization probe and the double-stranded DNA binding dye of each of the amplicons in the nucleic acid samples varying with cycle number is respectively measured. In the present embodiment, a graph as shown in FIG. 2 is illustrated. In FIG. 2, the top graph shows the fluorescence intensity of the hybridization probe varying with cycle number, and the bottom graph shows the fluorescence intensity of the double-stranded DNA binding dye varying with cycle number. The two are aligned and juxtaposed so as to be described in a subsequent process. It should be mentioned that, although FIG. 2 only shows three groups of amplicon curves, the graph shown in FIG. 2 only exemplarily illustrates the present embodiment, and the invention is not limited thereto. The number of experimental groups of the amplicon and the number of curves shown can be adjusted according to actual experimental conditions.

Then, referring to both FIG. 1 and FIG. 2, step S140 is performed, in which a threshold value T is defined in the fluorescence intensity measured for the hybridization probe. As shown in FIG. 2, the threshold value T is the fluorescence intensity value of the hybridization probe during the phase in which the fluorescence intensity of the hybridization probe is gradually increased as cycle number is increased. In the present embodiment, the threshold value T is, for instance, 1.1 to 1.5, but the invention is not limited thereto, and a suitable value as the threshold value T can also be defined in a phase in which the fluorescence intensity of the hybridization probe is gradually increased (i.e., linear phase) according to actual experimental conditions.

Referring to both FIG. 1 and FIG. 2, step S150 is performed, in which threshold cycle numbers C1, C2, and C3 of each of the amplicons in the nucleic acid samples are correspondingly obtained when the fluorescence intensity of the hybridization probe is the threshold value T. The reaction principle of the hybridization probe is that one fluorescence signal is emitted every time an amplicon is replicated, that is, the fluorescence intensity of the hybridization probe is positively related to the concentration of amplicon. However, the qPCR reaction amplification efficiency of each of the amplicons in the nucleic acid samples may be different (based on the difference in content of GC base), and therefore the measured concentration of each of the amplicons may still be different at the same cycle number. Therefore, the threshold value T is defined in the fluorescence intensity of the hybridization probe, so that the measured concentration of each of the amplicons can be normalized such that the concentration of each of the amplicons will be identical. That is, the concentration of each of the amplicons at the threshold cycle numbers C1, C2, and C3 is identical.

Referring to both FIG. 1 and FIG. 2, step S160 is performed, in which individual fluorescence intensities F1, F2, and F3 of the double-stranded DNA binding dye of each of the amplicons at the threshold cycle numbers C1, C2, and C3 are correspondingly obtained. Since the mechanism of reaction of the double-stranded DNA binding dye includes binding with amplicon and then embedding into double-stranded nucleic acid, greater length of amplicon translates to greater amount of the double-stranded DNA binding dye binding and embedding, which results greater fluorescence intensity. That is, the fluorescence intensity of the double-stranded DNA binding dye is positively correlated with the length of amplicon. As described above, the concentration of each of the amplicons at the threshold cycle numbers C1, C2, and C3 is the same, and therefore step S160 can obtain the individual fluorescence intensities F1, F2, and F3 of the double-stranded DNA binding dye of each of the amplicons when the concentration of each of the amplicons is the same.

Lastly, referring to FIG. 1 and FIG. 2, step S170 is performed, in which the individual fluorescence intensities F1, F2, and F3 are substituted in the linear regression curve of the fluorescence intensity of the double-stranded DNA binding dye and amplicon length to calculate the length of each of the amplicons. Regarding the linear regression curve of the fluorescence intensity of the double-stranded DNA binding dye and the amplicon length and detailed calculation steps, a known technique in the art can be adopted, and are therefore not repeated herein. As described above, step S160 can obtain the individual fluorescence intensities F1, F2, and F3 of the double-stranded DNA binding dye of each of the amplicons when the concentration of each of the amplicons is the same, and therefore step S170 can accurately measure the length of each of the amplicons when the concentration of each of the amplicons is the same.

Figure 3:
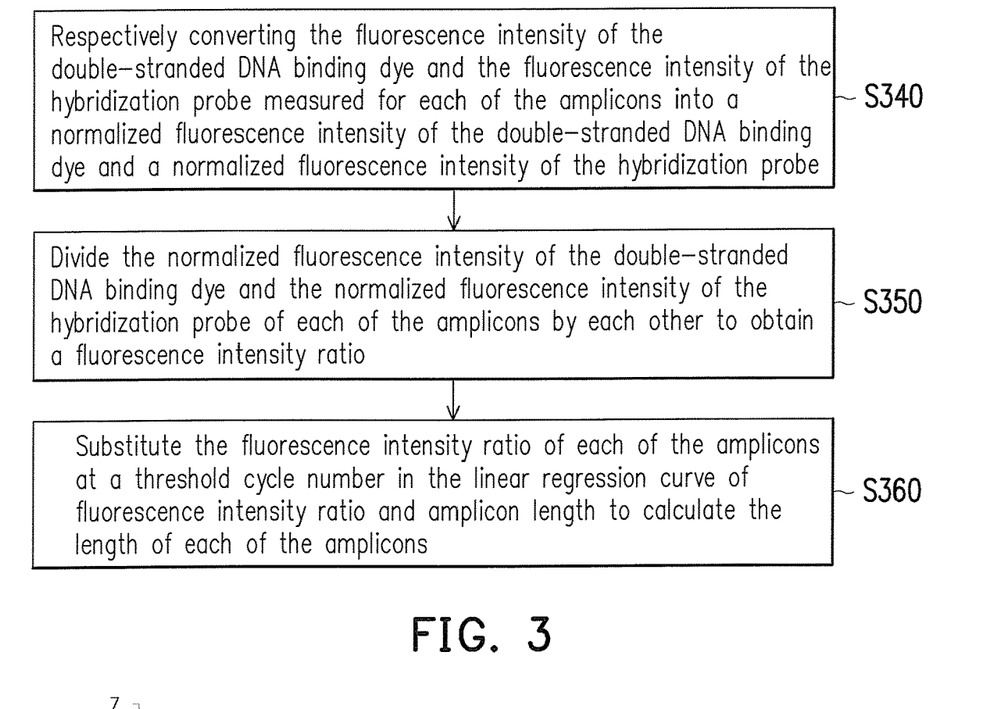
FIG. 3 is a schematic flow chart of a measuring method for amplicon length according to another embodiment of the invention.
Figure 4:
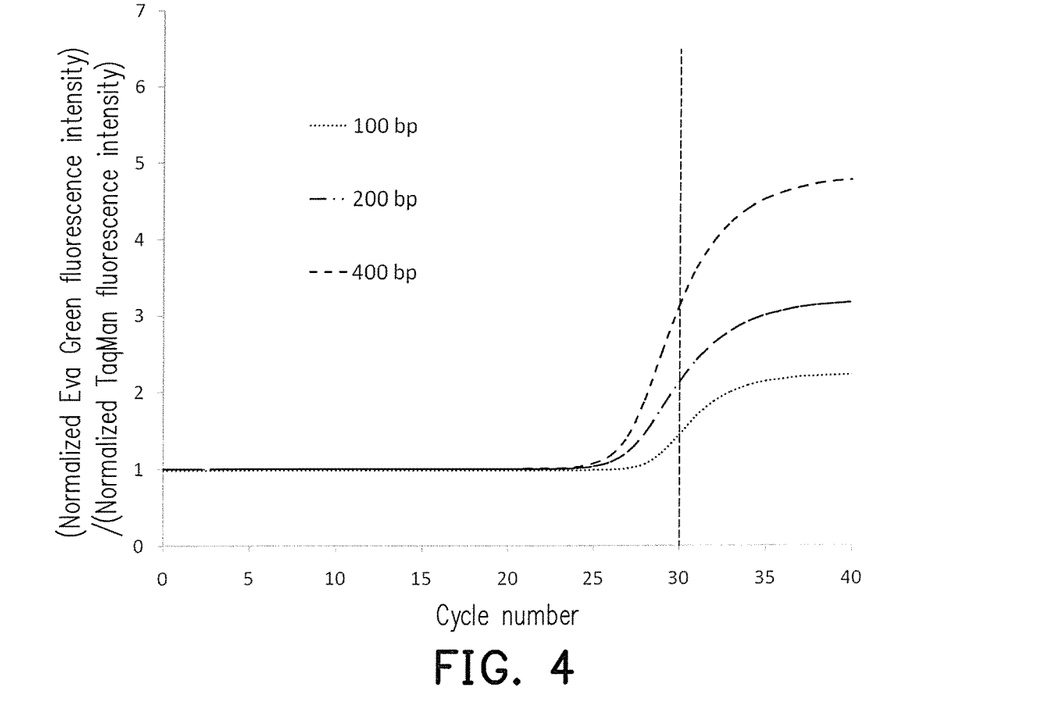
FIG. 4 is a graph of fluorescence intensity ratio of normalized Eva Green fluorescence intensity and normalized TaqMan fluorescence intensity varying with cycle number measured in the measuring method for amplicon length according to another embodiment of the invention.

FIG. 3 is a schematic flow chart of a measuring method for amplicon length according to another embodiment of the invention. FIG. 4 is a graph of fluorescence intensity ratio of normalized Eva Green fluorescence intensity and normalized TaqMan fluorescence intensity varying with cycle number measured in the measuring method for amplicon length according to another embodiment of the invention.

It should be mentioned that, the embodiments shown in FIG. 3 and FIG. 4 are similar to the embodiments shown in FIG. 1 and FIG. 2. The similarity is, in the embodiments shown in FIG. 3 and FIG. 4, step S110, step S120, and step S130 shown in FIG. 1 are also performed. The difference between the present embodiment and the above embodiments is that, after step S130 is performed, step S140, step S150, step S160, and step S170 in the above embodiments are not performed in the present embodiment, and instead step S340, step S350, and step S360 are performed. Since the details of step S110, step S120, and step S130 are provided in the above, the details of step S110, step S120, and step S130 are not repeated herein. Therefore, in the following, only step S340, step S350, and step S360 are described.

Referring first to FIG. 3, step S340 is performed, in which the fluorescence intensity of the double-stranded DNA binding dye and the fluorescence intensity of the hybridization probe measured for each of the amplicons are respectively converted into a normalized fluorescence intensity of the double-stranded DNA binding dye and a normalized fluorescence intensity of the hybridization probe. More specifically, the converting method of the normalized fluorescence intensity of the double-stranded DNA binding dye can include dividing the fluorescence intensity of the double-stranded DNA binding dye of each cycle by an average fluorescence intensity of the double-stranded DNA binding dye in a cycle interval to obtain the normalized fluorescence intensity of the double-stranded DNA binding dye. Moreover, the converting method of the normalized fluorescence intensity of the hybridization probe includes dividing the fluorescence intensity of the hybridization probe at each cycle by the average fluorescence intensity of the hybridization probe in the cycle interval to calculate the normalized fluorescence intensity of the hybridization probe. In the present embodiment, the cycle interval is, for instance, the third cycle to the eighth cycle in the baseline region in which the fluorescence intensity has not yet increased, but the invention is not limited thereto, and a suitable cycle interval can also be defined in the baseline region according to actual experimental conditions.

Then, referring to both FIG. 3 and FIG. 4, as shown in FIG. 3, step S350 is performed, in which the normalized fluorescence intensity of the double-stranded DNA binding dye and the normalized fluorescence intensity of the hybridization probe of each of the amplicons are divided by each other to obtain a fluorescence intensity ratio. In the present embodiment, a graph as shown in FIG. 4 can be illustrated, wherein the fluorescence intensity ratio is shown to vary with cycle number. It should be mentioned that, although FIG. 4 only shows three groups of amplicon curves, the graph shown in FIG. 4 only exemplarily illustrates the present embodiment, and the invention is not limited thereto. The number of experimental groups of the amplicon and the number of curves shown can be adjusted according to actual experimental conditions, and the length of the amplicon and the types of the double-stranded DNA binding dye and the hybridization probe used are also not limited thereto.

Then, referring to both FIG. 3 and FIG. 4, as shown in FIG. 3, step S360 is performed, in which the fluorescence intensity ratio of each of the amplicons at the threshold cycle number is substituted in the linear regression curve of fluorescence intensity ratio and amplicon length to calculate the length of each of the amplicons.

In the present embodiment, the threshold cycle number can be 25 to 35. In FIG. 4, the threshold cycle number is, for instance, 30, but the invention is not limited thereto, and a corresponding and suitable cycle number as the threshold cycle number can also be defined during the phase when the fluorescence intensity ratio is gradually increased (i.e., linear phase) according to actual experimental conditions. As shown in FIG. 4, when the threshold cycle number is 30, the fluorescence intensity ratio of 100 bp amplicon is 1.4, the fluorescence intensity ratio of 200 bp amplicon is 2.1, and the fluorescence intensity ratio of 400 bp amplicon is 3.1. Then, the aforementioned fluorescence intensity ratios are substituted in the linear regression curve of fluorescence intensity ratio and amplicon length to calculate the length of each of the amplicons.

In the following, the measuring method for amplicon length in the above embodiments is described in detail with an experimental example. However, the following experimental example is not intended to limit the invention.

Experimental Example

To prove that the measuring method for amplicon length provided by the invention is capable of accurately and simultaneously analyze both the length and the concentration of amplicon in nucleic acid samples, the following experimental example is provided.

A qPCR reaction mixture was added in the reaction wells of a test slide, and the contents of the components of the qPCR reaction mixture are as shown in Table 1 below. The nucleic acid samples are standard products for which amplicon length is known, and contain amplicons having lengths of 100 bp (base pair), 200 bp, 400 bp, and 800 bp. Then, a qPCR reaction was performed on the qPCR reaction mixture in the reaction wells.

TABLE 1

| Composition | Additive amount (μL) | Final concentration |
| --- | --- | --- |
| 2 × qPCR master mix | 30 | 1× |
| 2.5 uM forward primer | 3 | 0.125 uM |
| 2.5 uM reverse primer | 3 | 0.125 uM |
| 10 uM TaqMan probe | 3 | 0.5 uM |
| 40 × Eva Green dye | 3 | 2.5 uM |
| NGS library | 6 | |

The total reaction volume is increased to 60 μL with deionized water.

Figure 5:
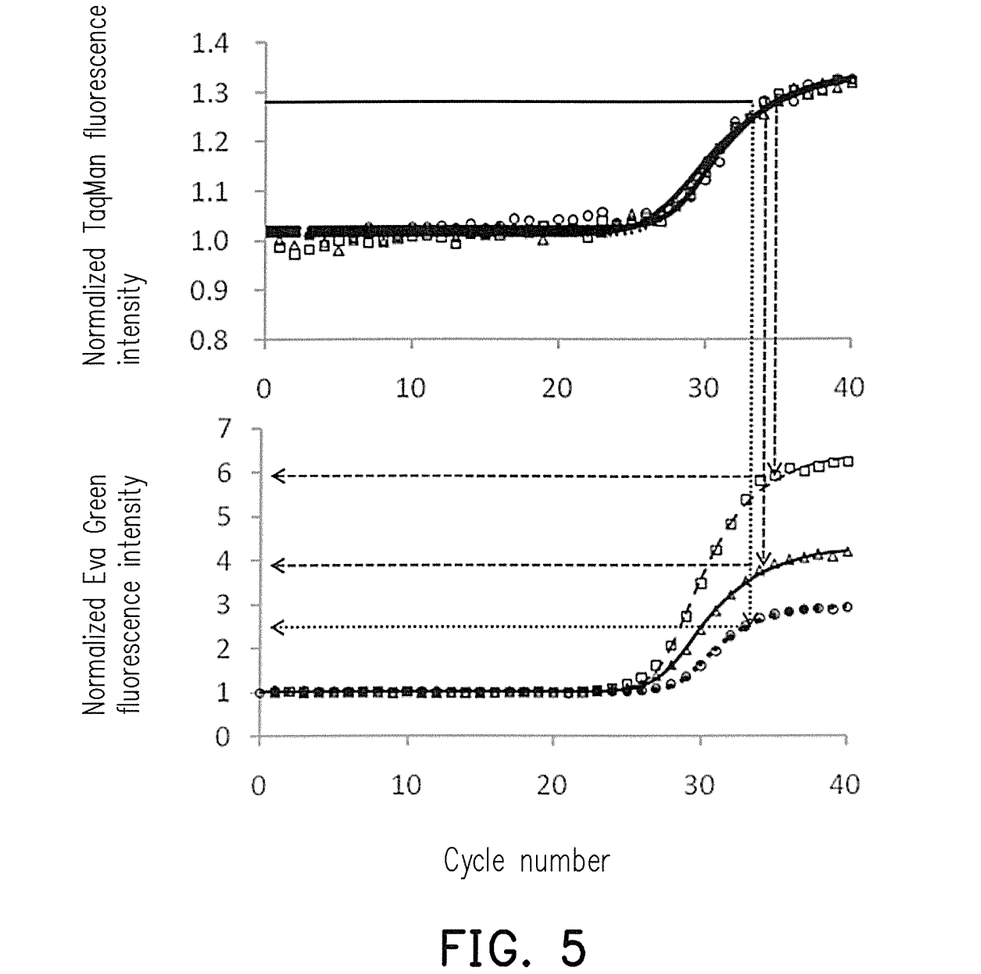
FIG. 5 is a graph of fluorescence intensity of each of a TaqMan probe and an Eva Green dye varying with cycle number measured in the experimental example according to an embodiment of the invention in which a measuring method for amplicon length is applied.

FIG. 5 is a graph of fluorescence intensity of each of a TaqMan probe and an Eva Green dye varying with cycle number measured in the experimental example according to an embodiment of the invention in which a measuring method for amplicon length is applied. In FIG. 5, the top graph shows the fluorescence intensity of the TaqMan probe varying with cycle number, and the bottom graph shows the fluorescence intensity of the Eva Green dye varying with cycle number, wherein each point represents one cycle.

Referring to FIG. 5, a threshold value of 1.3 is defined in the fluorescence intensity measured for the TaqMan probe, wherein the threshold value of 1.3 is a fluorescence value during a phase when the fluorescence intensity is gradually increased as the cycle number is increased. Then, the threshold cycle number of each of the amplicons is correspondingly obtained when the fluorescence intensity of the TaqMan probe is the threshold value of 1.3. Then, the individual fluorescence intensity of the Eva Green dye of each of the amplicons at the threshold cycle number is correspondingly obtained. As shown in FIG. 5, the fluorescence intensity of the Eva Green dye for the 100 bp amplicon is 3, the fluorescence intensity of the Eva Green dye for the 200 bp amplicon is 4, and the fluorescence intensity of the Eva Green dye for the 400 bp amplicon is 6. Then, the individual fluorescence intensities of the Eva Green dye are substituted in the linear regression curve of the fluorescence intensity of the Eva Green dye and amplicon length to calculate the length of each of the amplicons.

Figure 6:
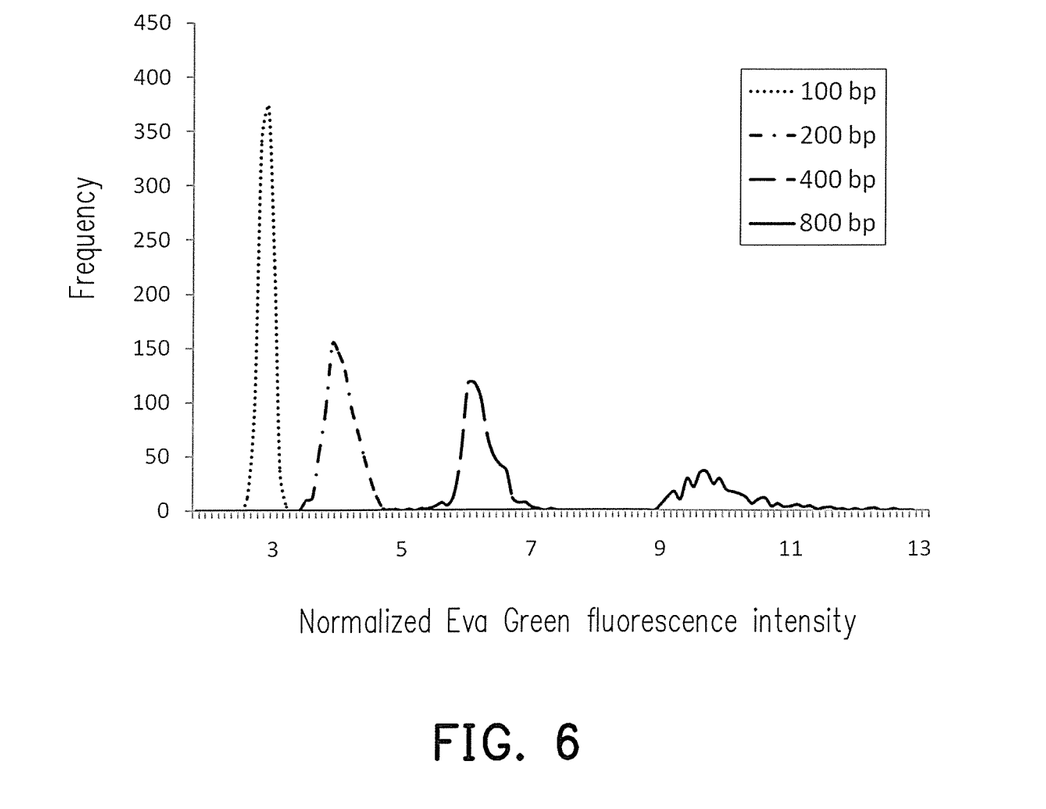
FIG. 6 is a histogram of normalized Eva Green dye fluorescence intensities of amplicons having different lengths in the experimental example according to an embodiment of the invention in which a measuring method for amplicon length is applied.

FIG. 6 is a histogram of normalized Eva Green dye fluorescence intensities of amplicons having different lengths in the experimental example according to an embodiment of the invention in which a measuring method for amplicon length is applied. Referring to FIG. 6, the 100 bp amplicon, the 200 bp amplicon, the 400 bp amplicon, and the 800 bp amplicon are clearly divided into four large areas separated from one another. Therefore, it can be known that the measuring method for amplicon length provided by the invention can accurately distinguish the length of each of the amplicons when the concentration of each of the amplicons is the same.

Figure 7:
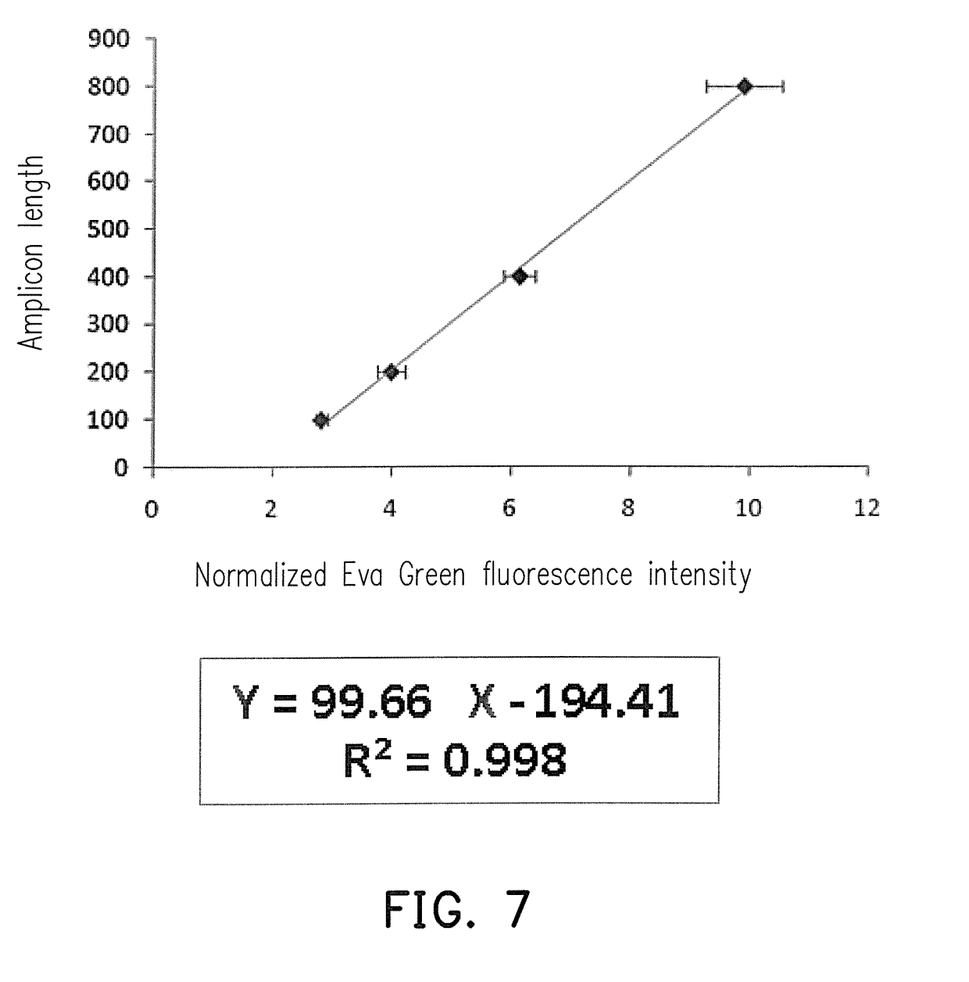
FIG. 7 is a graph of normalized fluorescence intensity of an Eva Green dye and amplicon length in the experimental example according to an embodiment of the invention in which a measuring method for amplicon length is applied.

FIG. 7 is a graph of normalized fluorescence intensity of the Eva Green dye and amplicon length in the experimental example according to an embodiment of the invention in which a measuring method for amplicon length is applied. FIG. 7 is a plot of the length of each of the amplicons corresponding to the average value of the fluorescence intensity of the Eva Green dye respectively measured with the 100 bp amplicon, the 200 bp amplicon, the 400 bp amplicon, and the 800 bp amplicon in the above experimental example. As shown in FIG. 7, a straight line having an almost smooth outline is obtained, and $R^2$ is 0.998, which is very close to 1. Therefore, it can be known that the measuring method for amplicon length provided by the invention can accurately measure the length of each of the amplicons when the concentration of each of the amplicons is the same.

Based on the above, since the measuring method for amplicon length provided by the invention adopts two types of dyes (hybridization probe and double-stranded DNA binding dye) at the same time to perform a qPCR reaction, the length of each of the amplicons can be accurately measured. Moreover, since a qPCR reaction is performed on the nucleic acid samples in an extremely-diluted range, the concentration can be calculated with a statistical distribution principle, and therefore sequence dilution does not need to be performed to make a standard curve. As a result, the measuring method provided by the invention only needs a small amount of nucleic acid samples for application, and has fewer detection restrictions. Therefore, the method of the invention can simultaneously analyze both the length and the concentration of amplicon in the nucleic acid samples in the same qPCR experiment, and can be applied in the quality control of NGS technique or any other related application of the molecular biology field requiring the accurate analysis of both length and concentration of amplicon in nucleic acid samples.

Although the invention has been described with reference to the above embodiments, it will be apparent to one of ordinary skill in the art that modifications to the described embodiments may be made without departing from the essence of the invention. Accordingly, the scope of the invention is defined by the attached claims not by the above detailed descriptions.

What is claimed is:

1. A measuring method for amplicon length, comprising:
mixing a qPCR master mix, a forward primer, a reverse primer, a hybridization probe, a double-stranded DNA binding dye, and nucleic acid samples to form a qPCR reaction mixture;
distributing the qPCR reaction mixture in reaction wells of a test slide, wherein no more than one of the nucleic acid samples is distributed in each of the reaction wells;
performing a qPCR reaction on the qPCR reaction mixture to respectively measure the fluorescence intensity of each of the hybridization probe and the double-stranded DNA binding dye of each amplicon in the nucleic acid samples varying with cycle number; and
applying a calculating method to calculate a length of each of the amplicons,
wherein the calculating method comprises:
defining a threshold value in the fluorescence intensity of the hybridization probe measured for each of the amplicons, and correspondingly obtaining a threshold cycle number of each of the amplicons when the fluorescence intensity of the hybridization probe is the threshold value;
correspondingly obtaining the individual fluorescence intensity of the double-stranded DNA binding dye of each of the amplicons at the threshold cycle number; and
substituting the individual fluorescence intensities in a linear regression curve of the fluorescence intensity of the double-stranded DNA binding dye and amplicon length to calculate a length of each of the amplicons,
wherein a concentration of the double-stranded DNA binding dye in the qPCR reaction mixture is 1 uM to 10 uM, a concentration of the hybridization probe in the qPCR reaction mixture is 0.2 uM to 1 uM, a concentration of the forward primer in the qPCR reaction mixture is 0.03 uM to 0.5 uM, and a concentration of the reverse primer in the qPCR reaction mixture is 0.03 uM to 0.5 uM.

2. The method of claim 1, wherein the threshold value is 1.1 to 1.5.

3. The method of claim 1, wherein the calculating method comprises:
respectively converting the fluorescence intensity of the double-stranded DNA binding dye and the fluorescence intensity of the hybridization probe measured for each of the amplicons into a normalized fluorescence intensity of the double-stranded DNA binding dye and a normalized fluorescence intensity of the hybridization probe;
dividing the normalized fluorescence intensity of the double-stranded DNA binding dye and the normalized fluorescence intensity of the hybridization probe of each of the amplicons by each other to obtain a fluorescence intensity ratio; and
substituting the fluorescence intensity ratio of each of the amplicons at the threshold cycle number in a linear regression curve of fluorescence intensity ratio and amplicon length to calculate the length of each of the amplicons.

4. The method of claim 3, wherein the converting method of the normalized fluorescence intensity of the double-stranded DNA binding dye and the normalized fluorescence intensity of the hybridization probe comprises:
dividing the fluorescence intensity of the double-stranded DNA binding dye at each cycle by an average fluorescence intensity of the double-stranded DNA binding dye in a cycle interval to obtain the normalized fluorescence intensity of the double-stranded DNA binding dye; and
dividing the fluorescence intensity of the hybridization probe at each cycle by the average fluorescence intensity of the hybridization probe in the cycle interval to obtain the normalized fluorescence intensity of the hybridization probe.

5. The method of claim 1, wherein the double-stranded DNA binding dye comprises an SYBR Green dye, an Eva Green dye, an LC Green dye, or an SYTO 9 dye.

6. The method of claim 1, wherein the qPCR master mix comprises a reaction buffer, dNTP, MgCl2, and Taq polymerase.

7. The method of claim 1, wherein a volume ratio of the nucleic acid samples and the qPCR reaction mixture is 1:60 to 1:10.

8. The method of claim 1, wherein the hybridization probe comprises a TaqMan probe, a molecular beacon probe, a dual-hybridization probe, or an Eclipse probe.

9. The method of claim 1, wherein the nucleic acid samples comprise a next-generation sequencing library.

10. The method of claim 1, wherein a concentration of the nucleic acid samples is 3 copies/µl to 30 copies/µl.

\* \* \* \* \*